United States Patent [19]

Wilkinson

[11] Patent Number: 5,267,150
[45] Date of Patent: Nov. 30, 1993

[54] INPUT ISOLATION CIRCUIT FOR COMPUTER-CONTROLLED MEDICAL DEVICE

[75] Inventor: Jeffrey D. Wilkinson, Vadnais Heights, Minn.

[73] Assignee: Medtronic, Inc., Minneapolis, Minn.

[21] Appl. No.: 741,289

[22] Filed: Aug. 7, 1991

[51] Int. Cl.[5] .............................................. H04M 1/21
[52] U.S. Cl. ..................... 364/413.02; 364/413.01; 364/413.03
[58] Field of Search ............... 364/413.01, 413.02, 364/413.03; 128/419 PT

[56] References Cited

U.S. PATENT DOCUMENTS

| | | | |
|---|---|---|---|
| 4,156,430 | 5/1979 | King et al. | 128/419 PT |
| 4,527,567 | 7/1985 | Fischler, et al. | 128/419 PT |
| 4,742,831 | 5/1988 | Silvian | 128/710 |
| 5,150,121 | 9/1992 | Newell et al. | 341/157 |

OTHER PUBLICATIONS

"Isolating Data-Converter Signals", *Electronic Design*, Jun. 28, 1990, p. 102.
"Ideas for Design", *Electronic Design*, Jun. 28, 1990, p. 104.

*Primary Examiner*—Roy N. Envall, Jr.
*Assistant Examiner*—Ari M. Bai
*Attorney, Agent, or Firm*—Dwight N. Holmbo; Harold R. Patton

[57] ABSTRACT

An apparatus for communicating an electrical signal from a first portion of circuitry to a second, wherein there is no direct electrical contact between the two portions. In one embodiment, an EKG transmitter is disclosed which receives surface EKG signals from a patient, amplifies the EKG signals, modulates an oscillating carrier signal with the EKG signals, and transmits the resulting modulated signal across an optocoupled boundary. The modulated signal is then digitized directly, without demodulation, using phase progression digitization. The digitized information, from which the patient's EKG signal may be reconstructed, is then transmitted via a modem over conventional telephone lines. DC power drawn from the telephone line may be used directly to power the modem and phase progression digitizer, and may also be coupled via an isolating DC-to-DC transformer, to the frequency modulator and amplifier. For components of the patient's EKG signal which cannot be accurately re-created after modulation, separate, isolated circuitry can detect and process these components prior to modulation, and a separate optocoupled boundary can be established for conveying information about these components to the modem or digitizer.

12 Claims, 6 Drawing Sheets

INPUT ISOLATION CIRCUIT FOR COMPUTER-CONTROLLED MEDICAL DEVICE

FIELD OF THE INVENTION

This invention relates generally to the field of computer-controlled medical devices, and more particularly to an isolation system for transmitting electrical signals between a patient and a computer-controlled medical device.

BACKGROUND OF THE INVENTION

In the field of computer-controlled medical devices, it is common to provide electrically isolated signal inputs for receiving electrical input signals from a patient. For example, computer-based programming devices for non-invasive programming of implantable cardiac pacemakers, cardioverters, defibrillators, and the like, often receive patient signals, such as surface EKG signals, from which the programmer can obtain information about the operation of the implanted device. Such a computer-based programming device may be powered by standard household current (e.g. 110-120 VAC), or by power derived from some other source, such as a battery or a telephone line. In order to ensure that there is no opportunity for the patient to receive an electrical shock due to a malfunction or short-circuit in the programmer, patient inputs are usually isolated from line-powered portions of the programmer circuitry by means of an isolation device. Typically, the input signals on one side of the isolation link are modulated (as by frequency modulation (FM), phase modulation (PM), pulse width modulation (PWM) or the like). The signal thus modulated is then passed across the isolation link, such as a conventional optocoupler/optoisolator device, commercially available from a number of semiconductor device manufacturers. At the other side of the isolation link, the signal is demodulated to restore its original format, and then converted to a digital representation using an analog-to-digital converter (ADC). The isolation link thus establishes a boundary between two portions of circuitry which are electrically isolated from one another, preventing the direct electrical conduction of electrical signals between the two isolated portions of circuitry.

A principle drawback of the prior techniques of electrical isolation of input circuits is the complexity of circuitry required to perform the demodulation and digitization of the modulated signal after it has passed across the isolation link. In addition, if the input signal to be modulated has high-frequency components, both the modulation and digitization circuitry must operate at correspondingly high rates in order to ensure that the original input signal can be accurately reconstructed upon digital-to-analog conversion and demodulation.

It is accordingly a feature of the present invention that analog electrical input signals received by a medical device are coupled to an electrical circuit and used to modulate an oscillating carrier signal in a manner in which the source of the electrical input signals remains electrically isolated from the electrical circuit.

It is a further feature of the present invention that after the modulated signal is passed across an isolation boundary, no demodulation is performed prior to digitization.

It is yet another feature of the present invention that the sampling rate for the digitization step is determined by the frequency content of the original analog input signal, not the frequency content of the modulated carrier signal.

It is yet another feature of the present invention that certain pre-processing of the original analog input signal prior to modulation is performed to extract information about certain high-frequency components of the input signal, such that the frequency of the modulated carrier signal and the sampling rate of the digitization may be minimized.

SUMMARY OF THE INVENTION

According to the present invention, an electrically isolated input signal, such as a patient's surface EKG signal, is amplified, filtered, modulated, and then passed across an isolation link. After passing across the link, the modulated signal is subjected to "phase progression digitization", as shall be hereinafter described, such that the analog characteristics of the isolated input signal are preserved in a digital format. The digitized signal may then be subjected to various forms of digital signal processing, transmitted across conventional digital data links, or stored in a digital storage medium for later retrieval. By eliminating the step of demodulating the modulated signal after passing across the isolation link, the complexity of the circuitry of the non-isolated circuitry in the medical device is greatly simplified.

Further in accordance with the present invention, the analog input signal is also applied to circuitry for detecting and measuring certain high-frequency components of the input signal, the output of this circuitry is coupled, via a separate isolation link, to the non-isolated circuitry.

In one embodiment of the invention, a medical device for transmitting EKG information onto a telephone line receives a patient's EKG signals on isolated inputs. The EKG signals are amplified, filtered, and then used to frequency-modulate an oscillating carrier signal. The modulated signal is then passed across an optoisolated link, where it is subjected to phase progression digitization. The digital information thus obtained is then transferred to a modem, which transmits the information onto the telephone line. The patient's EKG signal is also applied to circuitry for detecting and measuring pacemaker pacing pulse artifacts, with the output of this circuitry being coupled to the transmitter via a second optoisolated link.

BRIEF DESCRIPTION OF THE DRAWINGS

The foregoing and other features of the present invention will be best understood by reference to the detailed description of a specific embodiment, which follows, when read in conjunction with the accompanying drawings, wherein.

DETAILED DESCRIPTION OF A SPECIFIC EMBODIMENT OF THE INVENTION

Figure 1:
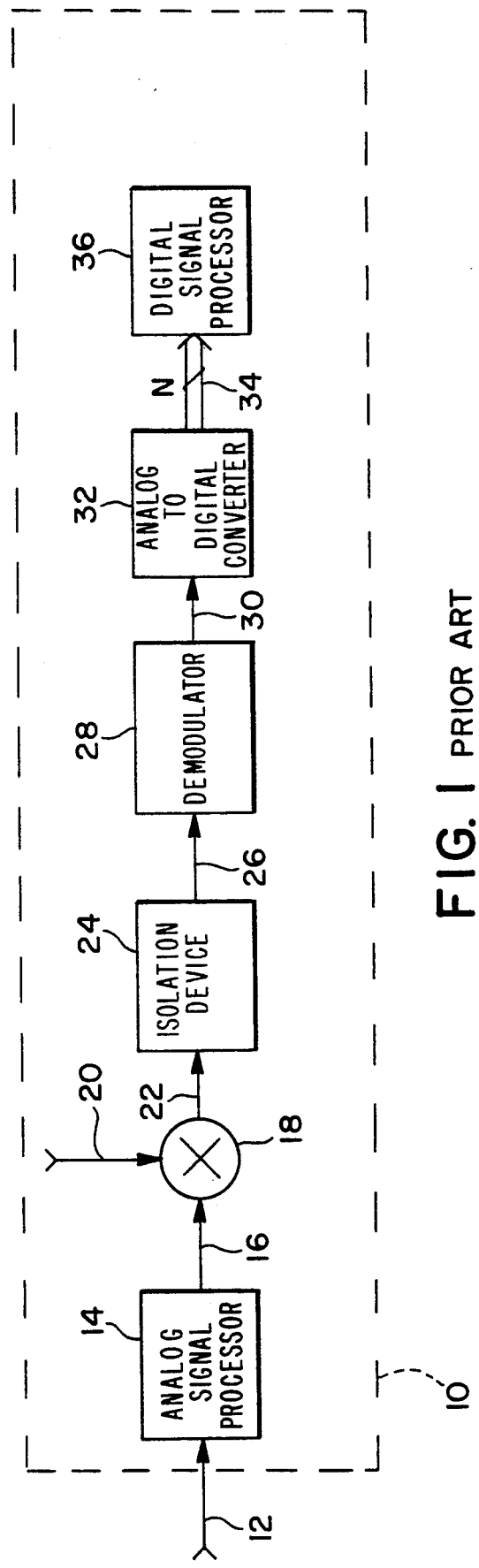
FIG. 1 is a block diagram of a prior art modulating-/digitizing system having isolated inputs.

FIG. 1 is a block diagram depicting a prior art technique for electrical isolation of patient leads from an external device. In FIG. 1, conductor 12 conducts an electrical signal, for example an EKG signal provided from electrodes attached to the surface of a patient's body, to an external device 10, which may be a pacemaker programmer, EKG monitor or the like. The signal on conductor 12 is applied to analog signal processing circuitry 14, which may perform such functions as filtering, conditioning, or amplification. The signal thus conditioned is next provided, on conductor 16, to a modulating device 18. Modulating device 18 receives a "carrier" signal on conductor 20 and, in a conventional manner, causes some characteristic of the carrier (e.g. frequency, phase, amplitude) to be modulated by the analog signal on conductor 16. In the case of frequency modulation, for example, modulation device 18 may be a voltage controlled oscillator, which varies the frequency of an oscillating carrier signal in response to variations in the amplitude of the modulating signal from conductor 16. The modulated signal is then provided, on conductor 22, to an isolation device 24.

Isolation device 24 may be any one of a number of known devices which are capable of transmitting analog signals from their inputs to their outputs without having a direct electrical connection therebetween. Such devices include relays, isolation transformers, and optocouplers. Thus, in FIG. 1, the modulated signal on line 22 is communicated onto conductor 26, even though there is no direct electrical connection between conductors 22 and 26.

The modulated signal on conductor 26 is then provided to demodulation circuitry 28, which re-creates the analog signal previously applied to the input of modulator 18. In the case of a frequency modulated signal, demodulator 28 produces an output signal on conductor 30 whose amplitude is determined at each point in time by the instantaneous frequency of the modulated signal at that time.

Finally, the re-created analog signal on conductor 30 is applied to an analog-to-digital converter (ADC) 32. As would be understood by one of ordinary skill in the art of digital circuitry, ADC 32 "samples" the amplitude of the analog input signal at regular intervals, and produces at each sample a multiple-bit binary number corresponding to the amplitude of the analog input signal at the time of that sample. It is well-known that in order for the analog signal to be accurately reconstructed from the digital output of an ADC, the frequency with which the ADC samples the analog input signal (the "sampling rate") must exceed the "Nyquist rate", which is defined as twice the frequency of the highest-frequency component of the analog signal. As a result, ADCs for high-frequency analog signals are typically complex and relatively expensive devices.

After the demodulated signal is digitized by ADC 32, the digital output (i.e. sequence of samples in the form of binary numbers) from ADC 32 may be provided, via digital data link 34, which may be a data path consisting of N conductors, where N is the number of bits in each binary sample produced by ADC 32, to digital signal processing circuitry 36.

As depicted in FIG. 1, isolation device 24 establishes a boundary between first and second isolated portions of circuitry, the first isolation portion including input lead 12, analog processing device 14 and modulation device 18, the second isolated portion of circuitry including demodulator 28, ADC 32, and digital signal processing circuit 36.

Figure 2:
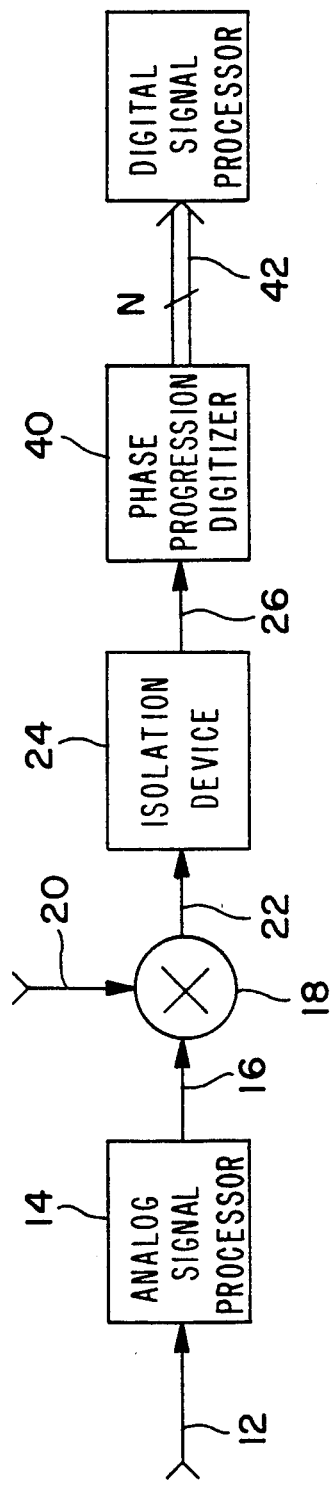
FIG. 2 is a block diagram of a modulating/digitizing system in accordance with the present invention.

Turning now to FIG. 2, an electrical isolation technique in accordance with one embodiment of the present invention is depicted, in which components which are the same as in FIG. 1 have retained like reference numerals. In FIG. 2, the signal to be isolated, e.g. an EKG signal from patient electrodes, is provided on conductor 12 to analog signal processing circuitry 14, and the processed signal provided on conductor 16 to modulating device 18. The modulated signal is then conducted across the isolation boundary to the second isolated portion of the circuitry in device 10. In FIG. 2, however, the modulated signal is not demodulated, but is instead provided directly to a phase progression digitizer 40, which digitizes the modulated signal provided on conductor 26, in a manner to be hereinafter described in greater detail. The digitized information derived from the modulated signal may then be provided via digital path 42 to digital signal processing circuitry 44 as required.

Figure 3A:
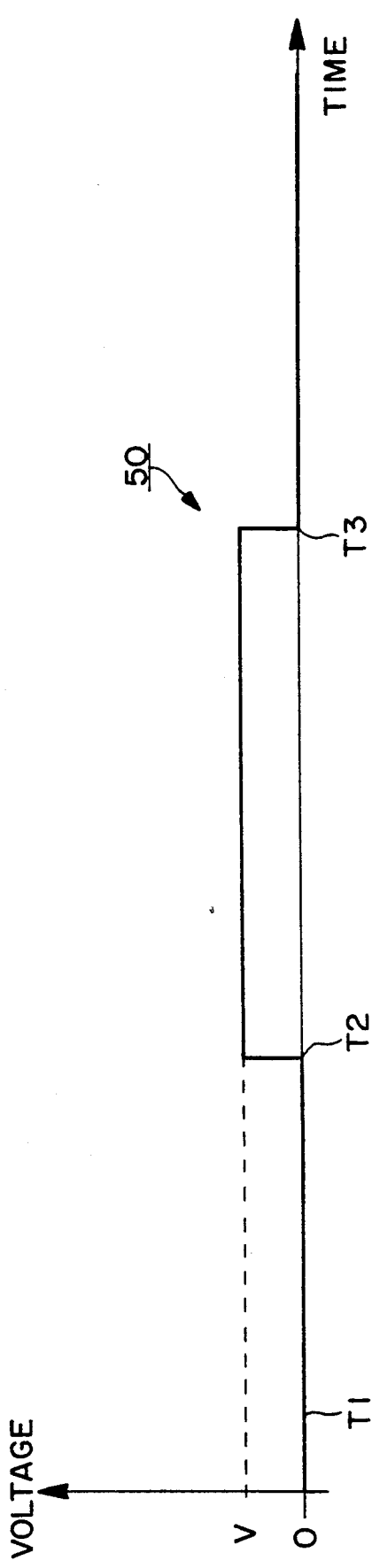
FIGS. 3a, 3b, and 3c are graphs of a modulating signal, a modulated signal, and the phase progression of the modulated signal, respectively.

The technique of phase progression digitization will now be described with reference to FIGS. 3a, 3b and 3c. In FIG. 3a, a simple voltage waveform to be digitized is designated generally as 50. The waveform 50 has a value of 0-volts at time T1, and stays at this 0-volt level until time T2. At time T2, the waveform assumes a value of V-volts, which is maintained until time T3 when the waveform returns to a 0-volt value. In accordance with the presently disclosed embodiment of the invention, the waveform 50 is first frequency modulated in a conventional manner, by means of a voltage-controlled oscillator described above with reference to FIG. The frequency-modulated carrier signal is designated generally as 60 in FIG. 3b. During the period between time T1 and time T2, the 0-volt value of waveform 50 has no modulating effect on waveform 60, which maintains a constant frequency from T1 to T2. When the value of waveform 50 rises to V-volts at time T2, however, the frequency of waveform 60 is correspondingly reduced, and stays at this reduced frequency until time T3, when waveform 50 returns to a 0-volt value and waveform 60 returns to its original frequency. The amplitude of waveform 60 oscillates between V1 (less than 0-volts) to V2 (greater than 0-volts), as shown in FIG. 3b.

Phase digitizing of the modulated waveform 60 is accomplished by sampling the signal at "upcrossings" (i.e., at points when waveform 60 crosses the V=0 axis). In particular, samples of waveform 60 occur at occasional upcrossings of waveform 60 at a relatively constant rate. In FIG. 3b, samples occur at the upcrossings designated as 64, 66, 68, 70, 72, 74, 76, 78, 80, 82, and 84 but do not occur at the upcrossings of waveform 60 designated as 86, 88, 90, 92, 94 or 96. As would be apparent to one of ordinary skill in electronics, the portion of waveform 60 between any two upcrossings (e.g. between upcrossings 66 and 88, or between upcrossings 88 and 68) constitutes one cycle of waveform 60. At the time of each sample, the current values of two continuously increasing variables are stored: the total cycle count, and the time stamp at that point. Every cycle of waveform 60 is counted, even those during which no sample is taken. Thus, for example, if the cycle beginning at upcrossing 62 and ending at upcrossing 64 is taken to be the first cycle of waveform 60, then the cycle beginning at upcrossing 64 and ending at upcrossing 86 is the second cycle of waveform 60, the cycle beginning with upcrossing 86 and ending at upcrossing 66 is the third cycle, and so on. When a sample does occur, the cycle number and the time of the sample are stored.

Figure 3B:
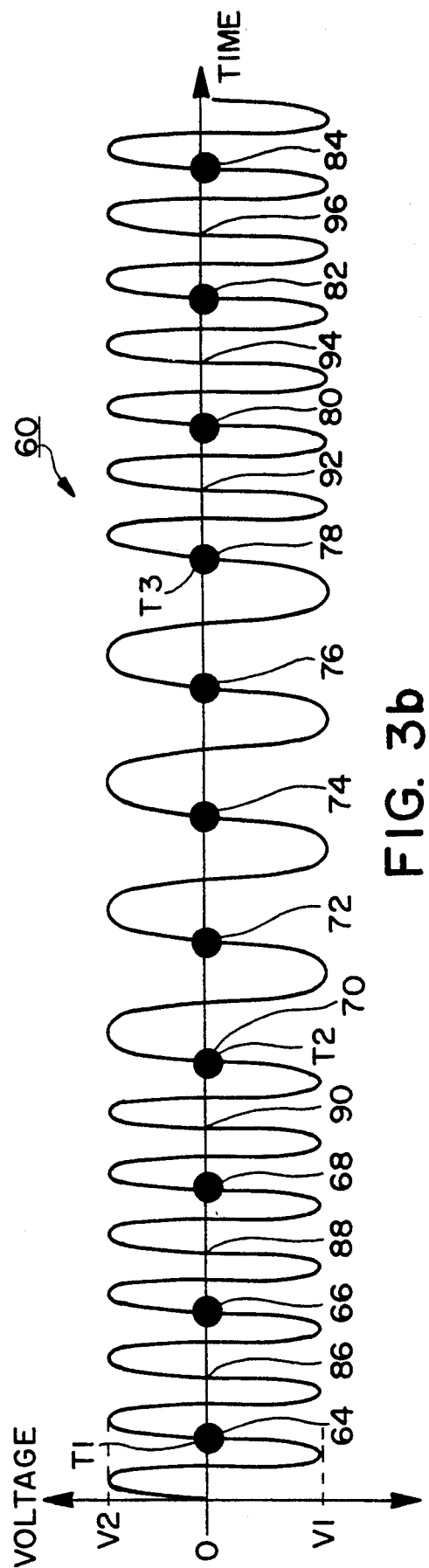

In the example depicted in FIGS. 3a and 3b, assume that the values stored at the time of each sample are as set forth in Table 1:

TABLE 1

| UPCROSSING NUMBER | CYCLE NUMBER | TIME (in nanoseconds) |
| --- | --- | --- |
| 64 | 1 | 0 |
| 66 | 3 | 20 |
| 68 | 5 | 40 |
| 70 | 7 | 60 |
| 72 | 8 | 80 |
| 74 | 9 | 100 |
| 76 | 10 | 120 |
| 78 | 11 | 140 |
| 80 | 13 | 160 |
| 82 | 15 | 180 |
| 84 | 17 | 200 |

Figure 3C:
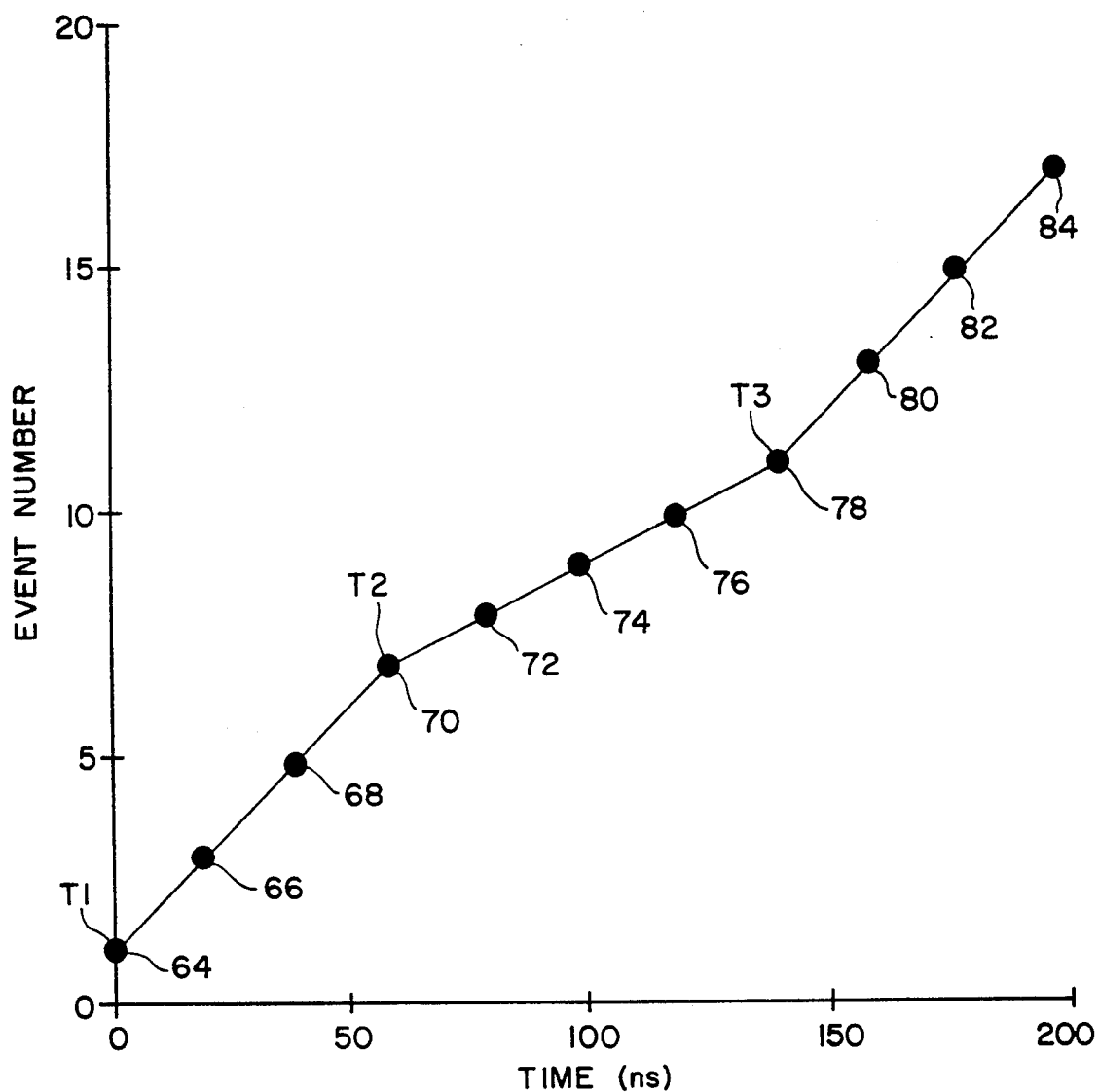

FIG. 3c is a graph of the sample values listed in Table 1 with time on the horizontal axis and the cycle number on the vertical axis. As can be seen from FIG. 3c, the slope of the line 100 formed by the samples indicates the frequency of the waveform 60, which in turn reflects the voltage of waveform 50. For example, during the period between time T2 and T3, the slope of the graph of FIG. 3c is less than the slope during the period from T1 to T2; thus, the lower the voltage of waveform 50, the greater the slope of the graph of FIG. 3c. In mathematical terms, the derivative of the function of FIG. 3c indicates the frequency of waveform 60 (FIG. 3b), which in turn indicates the amplitude of waveform 50 (FIG. 3a). As would be apparent to one of ordinary skill in mathematics, the slope of the graph of FIG. 3c between times T2 and T3 is 50, while the slope of the graph of FIG. 3c between times T1 and T2 is 100. Thus, the two data values associated with each sampling of the modulated signal can be used to re-create the original, unmodulated signal.

Figure 4:
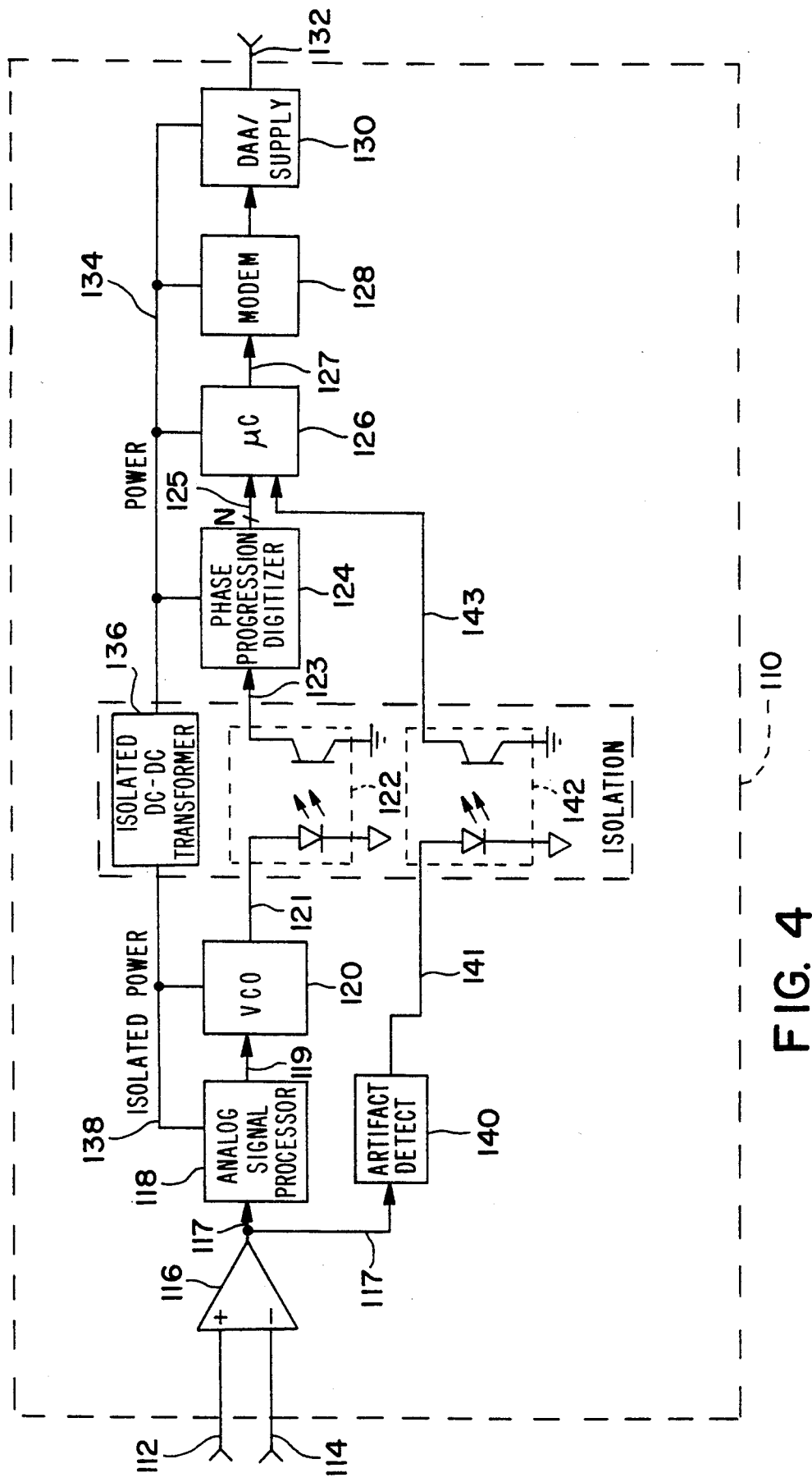
FIG. 4 is a block diagram of a trans-telephonic EKG transmitter in accordance with one embodiment of the present invention.

Turning now to FIG. 4, a more detailed diagram of an isolation scheme in accordance with the present invention is shown. In the embodiment of FIG. 4, the isolation and modulation scheme is employed in an EKG transmitter 110 as a method of coupling EKG signals from a patient to a conventional telephone line. In FIG. 4, EKG electrodes 112 and 114 are coupled to a patient in the conventional manner to receive the patient's EKG signals. Within EKG transmitter 110, the signals from EKG leads 112 and 114 are applied as the inputs to an analog amplifier 116. The output of amplifier 116 is applied, via conductor 117 to analog signal processing circuitry 118, which may include low-pass or band-pass filtering elements, signal clamping elements, and the like. The output from the analog signal processor, in turn, is coupled via conductor 119 to the input of a voltage-controlled oscillator 120, as previously described with reference to FIG. 1. The output from VCO 120 is applied via conductor 121 as an input to an optocoupler 122, which may be any one of a number of commercially available devices manufactured by such companies as Texas Instruments, Dallas, Tex.

The output of optocoupler 122 is applied via conductor 123 to a phase progression digitizer 124, the principle of operation of which was described above with reference to FIGS. 3a, 3b, and 3c. The digital output of phase progression digitizer 124 is provided on digital data path 125 as an input to a micro-controller 126. Microcontroller 126 may be implemented in various ways, including with a dedicated microprocessor or an application-specific integrated circuit (ASIC) or the like. Digital signals from microcontroller 126 are provided on conductor 127 to a modem 128, such as is conventionally used for communication of digital information over telephone lines. A DAA/Supply unit 130 provides an interface between modem 128 and telephone line 132. In addition, DAA/Supply unit 130 derives a supply voltage from telephone line 132. The techniques for provision of an interface between modem 128 and telephone line 132, as well as for deriving a supply voltage from telephone line 132 are well-known in the art of telephony, and will not be discussed in further detail herein.

The regulated supply voltage produced by DAA/Supply unit 130 is provided, via line 134, directly to all of the components in the second isolated portion of circuitry in EKG transmitter 110. In addition, supply line 134 is provided as an input to an isolating DC-to-DC transformer 136, in order that an isolated DC power supply can be provided, on line 138, to the components in the first isolated portion of circuitry in EKG transmitter 110.

When an analog signal is used to modulate a carrier signal, the frequency of the carrier signal must be sufficient to allow the analog signal to be accurately recreated through the process of demodulation. With a higher carrier frequency, more information about the modulating signal is preserved in modulation, and the modulating signal can be more accurately re-created upon demodulation. A lower carrier frequency can cause some distortion in the re-created modulating signal after demodulation of the carrier. Modulating signals with high frequency components require higher-frequency carrier signals than modulating signals with lower frequency content.

In the embodiment of FIG. 4, phase-progression digitization is employed to digitize an EKG signal. One instance where an EKG signal has a particularly high frequency content is during so-called pacing artifacts, which are received by the EKG electrodes when the patient's implanted pacemaker delivers a pacing pulse. For diagnostic purposes, it is often important to obtain an accurate measurement of the width (i.e. duration) of a pacing artifact; thus it is essential that the artifact not be distorted due to an insufficiently low carrier frequency. However, the use of higher frequency carrier signals necessitates a higher sampling rate of the phase-progression digitizer, making the implementation of the digitizer more complex and expensive.

In order to ensure the accurate measurement of pacing artifacts, the embodiment of FIG. 4 includes separate artifact detection and measurement circuitry 140 which receives the amplified EKG signal directly from the output of amplifier 116. With this arrangement, pacing artifacts are detected and measured in the unmodulated EKG signal, thereby increasing the accuracy of such measurements. In the embodiment of FIG. 4, the output of artifact detection and measurement circuit 140 is coupled via conductor 141 to a second optocoupler 142, the output of which is provided on conductor 143 to the non-isolated portion of device 110, and provided as an input to microcontroller 126. Since the pacing artifacts are typically the highest-frequency components of an EKG signal, detecting and measuring the artifacts prior to modulation of the EKG signal allows a lower-frequency carrier signal to be used in the modulation performed by VCO 120.

Figure 5:
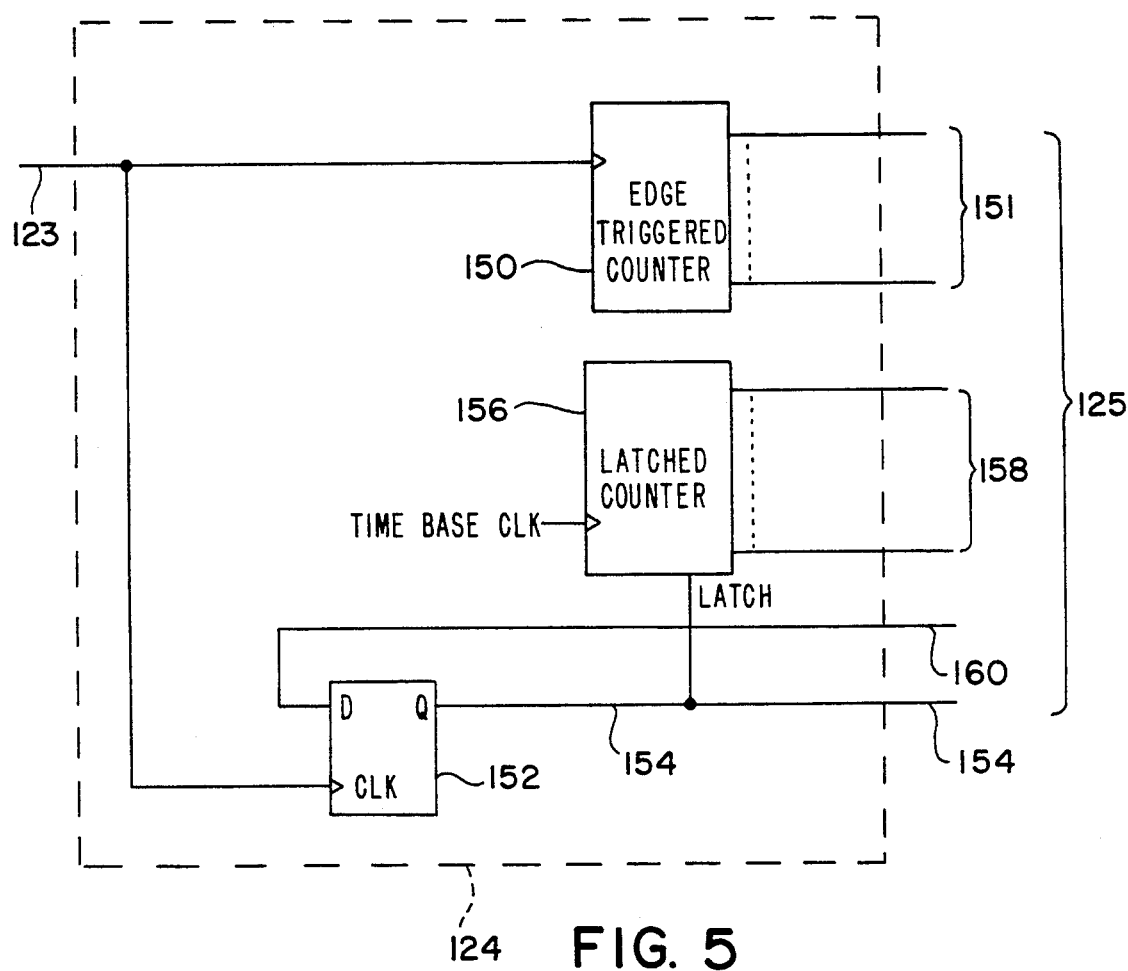
FIG. 5 is a block diagram of a phase progression digitizer from the embodiment of FIG. 4.

Turning now to FIG. 5, a block diagram of phase progression digitizer 124 from the embodiment of FIG. 4 is shown. The modulated signal passes across optocoupler 122 and is provided on line 123 to phase progression digitizer 124. Line 123 is coupled to the rising-edge triggered count input of a counter 150. With this arrangement, counter 150 increments its count value with each upcrossing of the modulated signal, thus providing at its output lines 151 the cycle number previously discussed with reference to FIGS. 3a, 3b, and 3c.

The modulated signal on line 123 is also provided to the clock input of a D flip-flop 152. The output of D flip=flop 152 is provided on line 154 to the LATCH input of a latched counter 156; line 154 is also provided as an output of phase progression digitizer 124. Latched counter 156 is clocked by a TIME BASE CLK signal of a known frequency which should exceed the frequency of the modulation carrier signal. The count value of counter 156 is provided on output lines 158.

The D input of D flip-flop 152 is provided on line 160 as an input to phase progression digitizer 124. The lines 151, 154, 158, and 160 collectively comprise the multiple-conductor digital data path 125 discussed above With reference to FIG. 4; these lines are coupled to microcontroller 126.

Operation of phase progression digitizer 124 is controlled by microcontroller 126. At some regular interval, microcontroller 126 asserts the signal on line 160, thus providing a positive input to D flip-flop 152. When the next upcrossing of the modulated signal appears on line 123, D flip-flop 152 will be triggered, causing the output signal on line 154 to go high. The high signal on line 154 will cause the current count value of counter 156 to be latched, thereby making a "time stamp" of the latest upcrossing. The signal on line 154 not only causes counter 156 to latch its current value, but also provides an indication to microcontroller 126 that an upcrossing has occurred. At this point, microcontroller 126 reads the count value of upcrossing counter 150 on lines 151, and the latched "time stamp" value on lines 158. As previously discussed with reference to FIGS. 3a, 3b, and 3c, the values on lines 151 and 158 are the event number and time stamp required for phase progression digitization sampling. Microcontroller 126 passes these value pairs to modem 128 for transmission on telephone line 132. A computer receiving these value pairs can then reconstruct the modulated EKG signal, as previously discussed with reference to FIGS. 3a, 3b, and 3c.

From the foregoing detailed description of a specific embodiment of the present invention, it should be apparent that a method and apparatus for electrically isolating inputs to an electronic circuit has been disclosed which employs phase progression digitization of a frequency modulated signal, thereby eliminating the steps of demodulation and analog-to-digital conversion. Although a specific embodiment has been disclosed in detail, it should be understood that various modifications, substitutions, or alterations may be made therein without departing from the spirit and scope of the appended claims, which follow.

In particular, it is contemplated that the isolation, modulation, and digitization of signals may have applicability in applications other than that disclosed, an EKG transmitter. In any situation in which signals are to be transmitted over some medium, it may be desirable to avoid any electrical interaction between the source of such signals and the transmission medium itself, both for the protection of the source of signals and for the transmission medium.

It is also contemplated that various alternative types of modulation, including phase shift keying, frequency shift keying, pulse burst width encoding or pulse burst interval encoding, may be employed instead of frequency modulation, as phase progression digitization is compatible with each of these forms of modulation.

What is claimed is:

1. An apparatus for transmitting a patient's surface EKG signals over a telephone line, comprising first and second portions of circuitry, said first and second portions being electrically isolated from one another, said first portion of circuitry comprising:

surface electrodes, attachable to a patient, for receiving the patient's EKG signal;

an amplifier for receiving, filtering, and amplifying said EKG signal;

modulating means for modulating a carrier signal with said amplified EKG signal, said modulating means producing a modulated signal;

first isolation means, receiving said modulated signal, for communicating said modulated signal to said second portion of circuitry;

said second portion of circuitry comprising:

a telephone modem, for transmitting digital information onto a telephone line;

interface means for establishing an interface between said modem and said telephone line, and for deriving a DC power supply signal from said telephone line;

phase digitization means, receiving said modulated signal from said isolation means, said phase digitization means producing, without demodulating said modulated signal, a digital signal comprising a digitized representation of said EKG signal wherein said phase digitization means comprises:

a binary counter defining a binary count value, said binary count value being incremented by one in response to an upcrossing of said isolated output signal, said binary counter producing a digital count signal corresponding to said binary count value, said digital count signal at a given time determining a current digital count signal at said given time;

a timer defining a binary timer value, said timer producing a digital time signal corresponding to said binary timer value, said digital time signal at a given time determining a current digital time signal at said given time; and a digital memory, for periodically storing said current digital count signal and said current digital time signal; and controller means for receiving said digital signal and communicating said digital output signal to said modem.

2. An apparatus in accordance with claim 1, wherein said first portion of circuitry further comprises:

means for detecting and measuring the pulse width of pacing artifacts, said means for detecting and measuring producing a first signal in response to the detection of a pacing artifact and a second signal corresponding to the pulse width of a detected pacing artifact.

second isolation means, for receiving said first and second signals and communicating said signals to said controller means.

3. An apparatus for transmitting electrical signals over a telephone line, comprising first and second portions of circuitry, said first and second portions being electrically isolated from one another, said first portion of circuitry comprising:

input means for receiving a raw electrical signal;

an amplifier for filtering, and amplifying said raw electrical signal;

modulating means for modulating a carrier signal with said amplified electrical signal, said modulating means producing a modulated signal;

first isolation means, receiving said modulated signal, for communicating said modulated signal to said second portion of circuitry;

said second portion of circuitry comprising: transmitting means, for transmitting digital information;

phase digitization means, receiving said modulated signal from said isolation means, said phase digitization means producing, without demodulating said modulated signal, a digital signal comprising a digitized representation of said raw electrical signal wherein said phase digitization means comprises:

a binary counter defining a binary count value, said binary count value being incremented by one in response to an upcrossing of said isolated output signal, said binary counter producing a digital count signal corresponding to said binary count value, said digital count signal at a given time determining a current digital count signal at said given time;

a timer defining a binary timer value, said timer producing a digital time signal corresponding to said binary timer value, said digital time signal at a given time determining a current digital time signal at said given time; and a digital memory, for periodically storing said current digital count signal and said current digital time signal; and controller means for receiving said digital output signal and communicating said digital output signals to said transmitting means.

4. An apparatus for receiving an isolated analog input signal and transmitting said signals over a transmission medium, said apparatus comprising:

an amplifier for amplifying and filtering said input signal, said amplifier producing an amplified output signal;

a modulator for modulating a carrier signal with said amplified output signal, said modulator producing a modulated output signal;

phase digitization means;

isolation means for communicating said modulated output signal across an electrical isolation boundary between said modulator and said phase digitization means;

said phase digitization means receiving said modulated output signal from said isolation means, said phase digitization means producing a sequence of binary digital values;

wherein said sequence of binary digital values is received by and transmitted over said transmission medium;

and wherein said sequence of binary digital values comprises a current digital count signal and a current digital time signal; and wherein said phase digitization means comprises:

a binary counter defining a binary count value, said binary count value being incremented by one in response to an upcrossing of said isolated output signal, said binary counter producing a digital count signal corresponding to said binary count value, said digital count signal at a given time determining said current digital count signal at said given time;

a timer defining a binary timer value, said timer producing a digital time signal corresponding to said binary timer value, said digital time signal at a given time determining said current digital time signal at said given time; and a digital memory, for periodically storing said current digital count signal and said current digital time signal.

5. An apparatus in accordance with claim 4, further comprising:

interface means for deriving a DC power supply signal from said transmission medium, said DC power supply signal being provided to said amplifier and said modulator.

6. An apparatus in accordance with claim 4, further comprising:

an high-frequency detection circuit, receiving said analog input signal, for detecting and measuring a high-frequency component of said analog input signal, said detection circuit producing a detection signal and a measurement signal, said detection signal for indicating the presence of said high-frequency component of said analog input signal and said measurement signal indicating a dimension of said high-frequency component;

second isolation means, for receiving said detection signal and said measurement signal, said second isolation means conveying said detection signal and said measurement signal to said transmission medium.

7. A method for transmitting an isolated analog input signal on a transmission medium, comprising the steps of:

(a) amplifying and filtering said analog input signal;

(b) modulating a carrier signal with said amplified and filtered analog input signal;

(c) conveying said modulated carrier signal across an electrical isolation boundary;

(d) phase digitizing said modulated carrier signal to produce a digital signal comprising a sequence of digital values, said sequence of digital values including a current digital count signal and a current digital time signal, said phase digitizing being performed on said modulated carrier signal after said modulated carrier signal has been conveyed across said electrical isolation boundary;

(e) storing said current digital count signal and said current digital time signal in a digital memory;

(f) transmitting said stored digital signal on said transmission medium; and (g) reconstructing said analog input signal from said transmitted digital signal;

wherein said analog input signal is electrically isolated from said transmission medium.

8. A method in accordance with claim 7, wherein said step of conveying said modulated carrier signal across said electrical isolation boundary comprises applying said modulated signal to an input of an optoelectronic coupling device.

9. A method in accordance with claim 7, wherein said step of transmitting said digital signal on said transmission medium comprises providing said digital signal to a telephone modem.

10. A method in accordance with claim 7, wherein said analog input signal is a human EKG signal.

11. An apparatus for electrically isolating first and second portions of circuitry, comprising:
- a modulator, for receiving an analog input signal and producing a modulated output signal;
- an isolation device, coupled to said modulator, for receiving said modulated output signal and producing an isolated output signal;
- a phase progression digitizer, coupled to said isolation device, for receiving said isolated output signal, said phase progression digitizer producing a digital output signal;

wherein said digital output signal comprises a digital representation of said analog input signal, and wherein said phase progression digitizer comprises:
- a binary counter defining a binary count value, said binary count value being incremented by one in response to an upcrossing of said isolated output signal, said binary counter producing a digital count signal corresponding to said binary count value, said digital count signal at a given time determining a current digital count signal at said given time;
- a timer defining a binary timer value, said timer producing a digital time signal corresponding to said binary timer value, said digital time signal at a given time determining a current digital time signal at said given time; and
- a digital memory, for periodically storing said current digital count signal and said current digital time signal.

12. An apparatus in accordance with claim 11, wherein said isolation device comprises an optoelectronic coupling device.

* * * * *